US009269027B1

(12) United States Patent
Khosla et al.

(10) Patent No.: US 9,269,027 B1
(45) Date of Patent: Feb. 23, 2016

(54) SYSTEM FOR OPTIMAL RAPID SERIAL VISUAL PRESENTATION (RSVP) FROM USER-SPECIFIC NEURAL BRAIN SIGNALS

(71) Applicant: HRL Laboratories, LLC, Malibu, CA (US)

(72) Inventors: Deepak Khosla, Camarillo, CA (US); David J. Huber, Calabasas, CA (US); Rajan Bhattacharyya, Sherman Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 178 days.

(21) Appl. No.: 14/185,908

(22) Filed: Feb. 20, 2014

Related U.S. Application Data

(60) Division of application No. 12/975,352, filed on Dec. 21, 2010, now Pat. No. 8,699,767, which is a continuation-in-part of application No. 12/214,259, filed on Jun. 16, 2008, now Pat. No. 8,363,939, which (Continued)

(51) Int. Cl.
*G06K 9/62* (2006.01)
*G06T 7/20* (2006.01)

(52) U.S. Cl.
CPC .............. *G06K 9/6267* (2013.01); *G06K 9/626* (2013.01); *G06T 7/2006* (2013.01)

(58) Field of Classification Search
CPC ............ G06K 9/46; G06K 2009/4666; G06K 9/4671; G06K 9/4676; G06K 9/6267; G06K 9/80; G06T 7/20; G06T 7/2006; G06T 2207/20021
See application file for complete search history.

(56) References Cited

U.S. PATENT DOCUMENTS

| | | | | |
|---|---|---|---|---|
| 6,670,963 | B2 | 12/2003 | Osberger | 345/629 |
| 7,835,581 | B2 | 11/2010 | Mathan et al. | 382/224 |
| 8,374,687 | B2 | 2/2013 | Mathan et al. | 600/544 |
| 2005/0047647 | A1 | 3/2005 | Rutishauser et al. | 382/159 |

(Continued)

FOREIGN PATENT DOCUMENTS

WO WO 03/093947 A2 11/2003

OTHER PUBLICATIONS

Andoni A., et al., "Near-Optimal Hashing Algorithms for Near Neighbor Problem in High Dimensions," Proceedings of the Symposium on Foundations of Computer Science (FOCS'06), 2006.

(Continued)

*Primary Examiner* — Andrew W Johns
(74) *Attorney, Agent, or Firm* — Tope-McKay & Associates

(57) ABSTRACT

Described is a system for optimizing rapid serial visual presentation (RSVP). A similarity metric is computed for RSVP images, and the images are sequenced according to the similarity metrics. The sequenced images are presented to a user, and neural signals are received to detect a P300 signal. A neural score for each image is computed, and the system is optimized to model the neural scores. The images are resequenced according a predictive model to output a sequence prediction which does not cause a false P300 signal. Additionally, the present invention describes computing a set of motion surprise maps from image chips. The image chips are labeled as static or moving and prepared into RSVP datasets. Neural signals are recorded in response to the RSVP datasets, and an EEG score is computed from the neural signals. Each image chip is then classified as containing or not containing an item of interest.

12 Claims, 8 Drawing Sheets

Related U.S. Application Data is a continuation-in-part of application No. 11/973,161, filed on Oct. 4, 2007, now Pat. No. 8,165,407, said application No. 12/975,352 is a continuation-in-part of application No. 12/316,779, filed on Dec. 16, 2008, now Pat. No. 8,214,309, and a continuation-in-part of application No. 12/653,561, filed on Dec. 15, 2009, now Pat. No. 8,285,052.

(60) Provisional application No. 60/944,042, filed on Jun. 14, 2007, provisional application No. 60/903,241, filed on Feb. 23, 2007, provisional application No. 60/849,975, filed on Oct. 6, 2006.

(56) References Cited

U.S. PATENT DOCUMENTS

| | | | | |
|---|---|---|---|---|
| 2007/0173699 A1 | 7/2007 | Mathan et al. | ................ | 600/300 |
| 2007/0236488 A1 | 10/2007 | Mathan et al. | ................ | 345/418 |
| 2008/0056611 A1 | 3/2008 | Mathan et al. | ................ | 382/284 |

OTHER PUBLICATIONS

Bentin, S., et al., "Electrophysiological studies of face perception in humans," Journal of Cognitive Neuroscience, 8, 551-565, 1996.
Berg A., "Shape matching and object recognition," Ph.D. thesis, UC Berkeley, Computer Science Division, Berkeley, CA, Dec. 2005.
Berka, C., et al., "Evaluation of an EEG-workload model in an aegis simulation environment" in Proceedings of SPIE Defense and Security Symposium, 90-99, 2005.
Bhattacharyya, R., et al., "Optimal image ordering for rapid serial visual presentation using electroencephalography," Presented at Society of NeuroScience (SfN) annual meeting, Chicago, 2009.
Carpenter G.A., et al., "A massively parallel architecture for a self-organizing neural pattern recognition machine," Computer Vision, Graphics, and Image Processing; 37, 54-115, 1987.
Carpenter G.A., et al., "The what-and-where filter a spatial mapping neural network for object recognition and image understanding," Computer Vision and Image Understanding, 69, 1-22, 1998.
Carpenter G.A., "Default ARTMAP," in Proc. of the International Joint Conference on Neural Networks (IJCNN'03), 1396-1401, 2003.
Carpenter G.A., et al., "Self-organizing information fusion and hierarchical knowledge discovery: a new framework using ARTMAP neural networks," Neural Networks, 18, 287-295, 2005.
Cowell, et al., "Construction and validation of neurophysio-technological framework for imagery artaiysis," in J.Jacke (Ed.): Human-Computer Interaction, Part II, HCII 2007, LNCS 4551, pp. 1096-1105, 2007, © Springer-Verlag Berlin Heidelberg.
Draper B., et al., "Evaluation at Selective Attention under Similarity Transforms," In Workshop on Performance and Attention in Computer Vision. Graz, Austria, Apr. 2003.
Eckhorn R., et al., "Coherent Oscillations: A Mechanism of feature linking in the visual cortex?" Biological Cybernetics 60, 121-130, 1988.
Eimer, M., "Does the face-specific N170 component reflect the activity of a specialized eye processor?" Neuroreport, 9, 2945-2948, 1998
Fabre-Thorpe M., et al., "A limit to the speed at processing in Ultra-Rapid visual categorization of novel natural scenes," Journal of Cognitive Neuroscience, 13, 171-180, 2001.
Field D. J., "Relations between the statistics of natural images and the response properties of cortical cells," J. Opt. Soc. Am. A., 4: 2379-2394, 1987.
Fei-Fei L., et al., "Learning generative visual models from few training examples: an incremental Bayesian approach tested on 101 object categories," CVPR 2004, Workshop on Generative-Model Based Vision, 2004.
Gerson, A.D., et al., "Cortically coupled computer vision for rapid image search ," IEEE Transaction on Neural Systems and Rehabilitation Engineering, 14(2): 174-179, Jun. 2006.
Gladwell, M., "Blink: the power of thinking without thinking," 1st ed. Little, brown and company: Time Warner Book Group, New York, 2005, pp. 18-47.
Gutin, G., et al., "Traveling salesman should not be greedy: domination of analysis of greedy-type heuristics for the TSP," Discrete Applied Mathematics, 117: 81-86, 2002.
Gray C.M., et al., "Oscillatory Responses in Cat visual cortex exhibit intercolumnar synchronization which reflects global stimulus properties," Nature 338: 334-336, 1989.
Hopf, J.-M., et al., "Localizing visual discrimination processes in time and space," The American Physiological Society, 88, 2088-2095, 2002.
Itti L., et al., "A saliency-based search mechanism for overt and covert shifts of visual attention," Vision Research, 40: 1489-1506, 2000.
Itti L., et al., "A Model of Saliency-Based Visual Attention for Rapid Scene Analysis," IEEE Transactions on Pattern Analysis and Machine Intelligence, 20, 1254-1259, 1998.
Itti L., et al., "Bayesian Surprise Attracts Human Attention," Vision Research 49: 1295-1306, 2008
Itti, L., et al., "Computational Modeling of Visual Attention," Nature Reviews Neuroscience, 2, 194-203, 2001.
Itti, L., "Quantifying the Contribution of low-level saliency to human eye movements in dynamic scenes," Visual Cognition, 12, 1093-1123, 2005.
Keysers, C., et al., "The Speed of Sight," Journal of Cognitive Neuroscience, 13(1), 90-101, 2001.
Khosla D., et al., "Bio-Inspired Visual Attention and Object Recognition," In: Proc. SPIE Defense, Security, and Sensing, 6560, 656003, 2007.
Khosla, D., et al., "A bio-inspired system for spatio-temporal recognition in static and video imagery," Proc. SPIE 6560, 656002, 2007.
Koch C., et al., "Shifts in selective visual attention: towards the underlying neual circuitry," Human Neurobiology, 4: 219-227, 1985.
Lazebnik S., et al., "Beyond Bags of Features: spatial pyramid matching for recognizing natural scene categories," In: Proc. IEEE Conference on Computer Vision and Pattern Recognition (CVPR), 2006.
Ling, H., et al., "Diffusion distance for histogram comparison," IEEE Computer Society Conference on Computer Vision and Pattern Recognition (CVPR), 2006.
Medasani, S., et al., "Possibilistic particle swarms for optimization," Proceedings 5673 of SPIE/IST Symposium on Electronic Imaging, 2005.
Medasani, S., et al., "Active learning system for object fingerprinting," International Joint Conference on Neural Networks, 2004.
Morrison, D., et al., "Semantic clustering of images using patterns of relevance feedback," in Proceedings of the 6th International Workshop on Content-based Multimedia Indexing (CBMI 2008), London, UK.
Nane S.A., et al., "Columbia Object Image Library (COIL-100)," Technical Report CUCS-006-96, Feb. 1996.
Navalpakkam V., et al., Modeling the Influence of Task on Attention, Vision Research, 45: 205-231, 2005.
NavalpakkamV., et al., "An integrated model of top-down and bottom-up attention for optimal object detection," In: Proc. IEEE Conference on Computer Vision and Pattern Recognition (CVPR), 1-7, 2006.
Navalpakkam V., et al., "Sharing resources: buy attention, get recognition," In: Proc. International Workshop on Attention and Performance in Computer Vision (WAPCV'03) Graz, Austria, Jul. 2003.
Navalpakkam, V., et al., "Search goal tunes visual features optimally," Neuron, 53, 605-617, 2007.
Niebur E., et al., "Control of selective visual attention modeling the 'where' pathway," In D. Touretzky, M Mozer and M. Hasselmo. Neural Imformation Processing Systems (NIPS 8), 802-808, Cambridge, MA, MIT, Press 1996.
Orabona F., et al., "Object-based Visual Attention: A Model for a Behaving Robot," In 3rd International Workshop on Attention and Performance in Computational Vision (in CVPR 2005), San Diego, CA, Jun. 2005.
Owechko, Y., et al., "A swarm-based volition/attention framework for object recognition," IEEE Conference on Computer Vision and Pattern Recognition, San Diego, 2005.

(56) References Cited

OTHER PUBLICATIONS

Owechko, Y., et al., "Cognitive swarms for rapid detection of objects and associations in visual imagery," IEEE Swarm Intelligence Symposium, 2005.
Peters, R.J. et al., "Beyond bottom-up: Incorporation task-dependent influences into computational model of spatial attention," in: Proc. IEEE Conference on Computer Vision and Pattern Recognition (CVPR), 2007.
Rogowitz, B.E., et al., "Preceptual image similarity experiments," Proceedings of SPIE, 3299: 576-590, 1998.
Scholl B.J., "Objects and Attention: the state of the art," Cognition 80, 1-46, 2001.
Serre T., et al., "Object recognition with features inspired by visual cortex," in Proceedings of the IEEE conference on computer vision and pattern recognition (CVPR), San Diego, CA, Jun. 2005.
Smeulders, A., et al., "Content-based image retrieval at the end of the early years," IEEE Transactions on PAMI, 22(12). 1349-1380, 2000.
Sun Y., et al., "Hierarchical selectivity for object-based visual attention," Submitted to Artificial Intelligence, 2004.
Office Action No. 1, for U.S. Appl. No. 12/975,352, mailed on Jul. 23, 2013.
Response to Office Action No. 1, for U.S. Appl. No. 12/975,352, filed Aug. 21, 2013.
Office Action No. 2, for U.S. Appl. No. 12/975,352, mailed on Sep. 25, 2013.
Response to Office Action No. 2, for U.S. Appl. No. 12/975,352, filed Nov. 25, 2013.
Thorpe, et al., "Speed of Processing in the Human Visual System", Nature, vol. 381, pp. 520-522, 1996.
Khosla, et al., "Optimal detection of objects in images and videos using elecroencephalograpy (EEG)," Proc. SPIE 8050, Signal Processing, Sensor Fusion, and Target Recognition XX, edited by Ivan Kadar, Proc. of SPIE vol. 8050 (May 4, 2011).
Raymond, et al., "Temporary suppression of visual processing in an RSVP task: an attentional blink?" Journal of experimental psychology, Human perception and performance 18 (3): pp. 846-860, 1992.
Rajan Bhattacharyya, Deepak Khosla, David Huber, Penn Tasinga, "Optimal Image Ordering for Rapid Serial Visual Presentation Using Electroencephalography," Sfn NeuroScience Oct. 17-21, 2009, Chicago, Poster Presentation, (2009).
Deepak Khosla, David J. Huber, Rajan Bhattacharyya, Mike Daily, Penn Tasinga, "Neurally Inspired Rapid Detection of Sparse Objects in videos," Signal Processing, Sensor Fusion, and Target Recognition XIX, Proc. of SPIE vol. 7697, 76971C, (2010).
Steven B. Most, Marvin M. Chun, David M. Widders and David H. Zald, "Attentional rubbernecking: Cognitive control and personality in emotion-induced blindness", Psychonomic Bulletin & Review. (2005) vol. 12, No. 4, 654-661, DOI: 10.3758/BF03196754.
Bernhard Hommel and Elkan G. Akyüre; Lag-1 sparing in the attentional blink:Benefits and costs of integrating two events into a single episode, The Quarterly Journal of Experimental Psychology (2005), 58A (8), 1415-143.
Nieuwenhuis S, Gilzenrat MS, Holmes BD, Cohen JD (Aug. 2005) "The role of the locus coeruleus in mediating the attentional blink: a neurocomputational theory". J Exp Psychol Gen 134 (3): 291-307. doi:10.1037/0096-3445.134.3.291. PMID 16131265.
Sun, Y., et al., "Probabilistic judgment by a coarser scale: behavioral and ERP evidence," in Proceedings of the Twenty-sixth Annual meeting of the Cognitive Science Society, 2004.
Thorpe, S., et al., "Speed of processing in the human visual system," Nature, vol. 381, pp. 520-522, 1996.
University of California, San Diego Complex Systems and Cognition Laboratory, CSCLAB Image Database http://csclab.ucsd.edu/labeledimages.php. 2006.
Walther D., et al, "Attentional selection for object recognition—a gentle way," Lecture Notes in Computer Science 2525: 472-479, 2002.
Wolfe J.M., "Visual Search in continuous, naturalistic stimuli," Vision Research 34: 1187-1195, 1994.
Vazirani, V., "Approximation Algorithms," Springer-Verlag, Berlin, Germany, pp. 32-33 (2004).
Vogel, E.K., et al., "The Visual NI Component as an index of a discrimination process," Psychophysiology, 2000.
Yamaguchi, S., et al., "Cerebral Asymmetry of the 'Top-down' allocation of attention to global and local features," The Journal of Neuroscience, 20, 1-5, 2000.
Zang H., et al., "SVM KNN: Discriminative nearest neighbor classification for visual category recognition," CVPR 2006.26.
http://en.wikipedia.org/Travelling_salesman_problem. Dec. 2, 2009.
Richard P. Wildes, "A measure of motion salience for surveillance applications" in Proc. IEEE Int'l Conf. Image Processing, 1998.

SYSTEM FOR OPTIMAL RAPID SERIAL VISUAL PRESENTATION (RSVP) FROM USER-SPECIFIC NEURAL BRAIN SIGNALS

PRIORITY CLAIM

This is a Divisional application of U.S. Non-Provisional application Ser. No. 12/975,352, filed on Dec. 21, 2010, entitled, "A System for Optimal Rapid Serial Visual Presentation (RSVP) from User-Specific Neural Brain Signals", which is a Continuation-in-Part application of U.S. Non-Provisional application Ser. No. 12/214,259, filed on Jun. 16, 2008, entitled, "Visual Attention and Segmentation System", which is a Continuation-in-Part application of U.S. Non-Provisional application Ser. No. 11/973,161, filed on Oct. 4, 2007, entitled, "Visual Attention and Object Recognition System", which is a Non-Provisional application of U.S. Provisional Application No. 60/944,042, filed on Jun. 14, 2007, entitled, "A Bio-inspired System for Visual Object-Based Attention and Segmentation", U.S. Provisional Application No. 60/903,241, filed on Feb. 23, 2007, entitled, "Bio-Inspired Vision System for Object Recognition", and U.S. Provisional Application No. 60/849,975, filed on Oct. 6, 2006, entitled, "Bio-Inspired Vision System for Object Recognition".

This is a Divisional application of U.S. Non-Provisional application Ser. No. 12/975,352, filed on Dec. 21, 2010, entitled, "A System for Optimal Rapid Serial Visual Presentation (RSVP) from User-Specific Neural Brain Signals", which is also a Continuation-in-Part application of U.S. Non-Provisional application Ser. No. 12/316,779, filed on Dec. 16, 2008, entitled, "Cognitive-Neural Method for Image Analysis".

Finally, this is a Divisional application of U.S. Non-Provisional application Ser. No. 12/975,352, filed on Dec. 21, 2010, entitled, "A System for Optimal Rapid Serial Visual Presentation (RSVP) from User-Specific Neural Brain Signals", which is also a Continuation-in-Part application of U.S. Non-Provisional application Ser. No. 12/653,561, filed on Dec. 15, 2009, entitled, "Image Ordering System Optimized Via User Feedback".

BACKGROUND OF THE INVENTION (1) Field of Invention

The present invention relates to an anomaly detection system and, more particularly, to a system for detecting anomalies in a series of images by optimizing rapid serial visual presentation (RSVP) from user-specific neural brain signals.

(2) Description of Related Art

Anomaly detection systems can be used to identify anomalies, or patterns that differ from an established normal behavior, in sets of data. Several techniques exist for identifying anomalies within a dataset. One such technique involves measuring the brain activity of a user monitoring a series of images for anomalies, known as rapid serial visual presentation (RSVP). RSVP measures the brain activity of a human subject while watching a stream of rapid images in order to find incongruities and inconsistencies in the images (i.e., "targets"). The RSVP protocol has recently been used as a powerful tool for high-throughput filtering of images into simple "target" and "non-target" categories as described by Thorpe et al. in "Speed of Processing in the Human Visual System" in *Nature*, vol. 381, pp. 520-522, 1996 (hereinafter referred to as the Thorpe reference), which is hereby incorporated by reference as though fully set forth herein. This involves displaying a series of small images (e.g., at 256-by-256 pixel resolution), called "chips" to a human subject at a very high frame rate (e.g., 10 Hertz) and measuring the electrical activity of the subject's brain using electroencephalograph (EEG) technology. Image transitions of high contrast can induce false alarm signals in the subject's brain, reducing the effectiveness of the experiment.

During a RSVP experiment, the images presented to the human subject are randomized. While this is often acceptable when presenting a subject with a sequence of images taken from satellite imagery, this poses problems when land-based imagery is employed. Artifacts of depth, such as lighting, scale, and texture changes, as well as topography variations (e.g., ground versus sky) provide a great deal more image variance, which leads to false positives in recording of neural brain signals (i.e., electroencephalography, or EEG) of the subject as the result of high contrasts in the features of quickly-presented image chips that cause undesired "surprise" EEG signals. A surprise EEG signal occurs when two contrasting non-target images are placed in immediate succession to one another.

Prior art exists to transform the images in a RSVP set to be similar to each other across certain perceptual factors. For example, images can be nonlinearly corrected via gamma transform to match their mean luminance in order to minimize the "jarring" effect as described by Gerson et al. in "Cortically Coupled Computer Vision for Rapid Image Search" in *IEEE Transactions on Neural Systems and Rehabilitation Engineering,* 14(2): 174-179, 2006 (hereinafter referred to as the Gerson reference), which is hereby incorporated by reference as though fully set forth herein. However, these methods exhibit limited success, and the image sequence presented by RSVP is still highly "jarring" to the user.

The next-best solution to this problem is in the field of content-based image retrieval (CBIR) which permits image searching based on features automatically extracted from the images themselves as described by Smeulders et al. in "Content-Based Image Retrieval at the End of the Early Years" in *IEEE Transactions on PAMI.* 22(12): 1349-1380, 2000 (hereinafter referred to as the Smeulders reference), which is hereby incorporated by reference as though fully set forth herein. The CBIR field has been motivated by the need to efficiently manage large image databases and run image retrievals without exhaustive searches of the image archive each time. The system compares the features of the selected image with the characteristics of the other images in the set and returns the most similar images. Typically, this is done by computing, for each image, a vector containing the values of a number of attributes and computing the distance between image feature vectors. Many different features and combinations have been used in CBIR systems. Color retrieval yields the best results, in that the computer results of color similarity are similar to those derived by a human visual system as described by Rogowitz et al., in "Perceptual Image Similarity" in *Proceedings of Society of Photo-Optical Instrumentation Engineers* (*SPIE*), 3299: 576-590, 1998 (hereinafter referred to as the Rogowitz reference), which is hereby incorporated by reference as though fully set forth herein. Features include texture, shape, and bio-inspired features, for example. The best image matches are typically returned and displayed to the user in descending order of the computed distance.

While CBIR could be naively applied to image ordering for the problem of EEG experimentation using RSVP, this would pose a number of difficulties that would make it inferior. For a block of images to be ordered for RSVP, one could determine the feature set of each and load them into the CBIR database. Starting from an arbitrary image, one could find the closest match, then the closest match to that image (the match), and so on, until all images have been queued. This procedure is equivalent to using the "nearest neighbor" heuristic for solving the travelling salesman problem (TSP), an NP-complete problem in combinatorial optimization. However, this algorithm does not guarantee the optimal result, and can actually provide the least optimal result depending on the dataset and the first image selected as described by Gutin et al. in "Traveling Salesman Should Not be Greedy: Domination Analysis of Greedy-Type Heuristics for the TSP in *Discrete Applied* Mathematics, 117: 81-86, 2002 (hereinafter referred to as the Gutin reference), which is hereby incorporated by reference as though fully set forth herein.

The prior art for user relevance feedback (i.e., supervised learning) in CBIR systems primarily focuses on whether the images returned by the algorithm are similar to a seed image as presented by Morrison et al. in "Semantic Clustering of Images Using Patterns of Relevance Feedback" in *Proceedings of the 6th International Workshop on Content-based Multimedia Indexing* (*CBMI* 2008), London, UK, 2008 (hereinafter referred to as the Morrison reference), which is hereby incorporated by reference as though fully set forth herein. This involves running the computer algorithm to find a candidate match for an image, and then allowing the user to answer as affirmative or negative regarding the similarity of the image. CBIR systems do not address the issue of image sequencing or determining the relative similarity of images that may, in fact, be very similar to one another. The CBIR prior art has no notion of ordering of the images. Each of the prior methods discussed above exhibit limitations that make them incomplete. This is because they generally do not directly address the problem of ordering images specifically for the RSVP method and consequently produce results that are unacceptable for the application.

In addition to optimizing RSVP for image ordering, the technique can also be used to optimize search and detection performance for items of interest (IOI) in images (static RSVP) and videos (video RSVP). Prior art exists which describes bio-inspired visual attention mechanisms for static RSVP. The first is a system that computes pure saliency on the frames of a video stream and reports possible targets based on those results. Systems using feature-based saliency have been proposed by Itti and Koch in "A saliency-based search mechanism for overt and covert shifts of visual attention" in *Vision Research,* 40: 1489-1506, 2000, and Navalpakkam and Itti in both "Modeling the Influence of Task on Attention" in *Vision Research,* 45: 205-231, 2005 and "An integrated model of top-down and bottom-up attention for optimal object detection" in *Proc. IEEE Conference on Computer Vision and Pattern Recognition* (*CVPR*), 1-7, 2006.

Secondly, object-based approaches have been proposed by Khosla et al. in "Bio-Inspired Visual Attention and Object Recognition" in *Proc. SPIE Defense, Security, and Sensing,* 6560, 656003, 2007, Draper and Lionelle in "Evaluation of Selective Attention under Similarity Transforms in *Workshop on Performance and Attention in Computer Vision*, Graz, Austria, April 2003, and Orabona et al. in "Object-based Visual Attention: A Model for a Behaving Robot" in 3rd *International Workshop on Attention and Performance in Computational Vision* (*in CVPR* 2005), San Diego, Calif., 2005. These systems run a saliency algorithm on the frames in a video stream and return a given number of possible targets based on their saliency in that frame. The pure surprise algorithms (both feature- and object-based) can yield poor results when applied to video imagery of a natural scene. Artifacts from ambient lighting and weather often produce dynamic features that can throw off a saliency algorithm and cause it to think that "everything is salient". Mathematically, it may be the case that everything in the scene is salient. However, when a system is tasked with a specific purpose, such as surveillance, one is only interested in legitimate short-term anomalies that are likely to be targets. Therefore, simple saliency systems cannot provide the service that the current invention does.

The alternative approach is to use a full surprise algorithm. These algorithms employ a great deal of additional processing on the features in each frame of the video and create statistical models that describe the scene. If anything unexpected happens, the surprise algorithm is able to return the location of the happening. The closest known prior art is the surprise algorithm of Itti and Baldi in "Bayesian Surprise Attracts Human Attention" in *Vision Research* 49: 1295-1306, 2008. This work employs a Bayesian framework and features that contribute to the saliency map to construct a prior distribution for the features in the scene. The current saliency map is used as the seed for a "posterior" distribution. The algorithm uses the KL distance between the prior and posterior as the measure of surprise. Because it takes the entire history of the scene into account, it exhibits a much lower false alarm rate than that of a system that exclusively uses saliency. However, as one might expect from the description of the algorithm, the Itti and Baldi surprise algorithm is very complicated and computationally expensive. It was designed to run on very high-end computer hardware and, even then, cannot currently run at real-time on high-resolution video imagery. The computer hardware it runs on is very bulky and power-consuming, which prevents its use on a mobile platform. Furthermore, the complexity of the algorithm largely prevents it from being ported to low-power hardware, which is essential for deployment on a mobile platform. In addition to the above, there are a plethora of non-saliency based methods that model the background and then use changes in this model to detect "change" regions. The prior art cited above are hereby incorporated by reference as though fully set forth herein.

Thus, a continuing need exists for an automated system for optimizing RSVP that addresses the issue of image sequencing or determining the relative similarity of images that may be very similar to one another based on user feedback. Additionally, a need exists for a system for optimizing search and detection performance for IOI in videos that use RSVP-based EEGs.

SUMMARY OF THE INVENTION

The present invention relates to an anomaly detection system and, more particularly, to a system for detecting anomalies in a series of images by optimizing rapid serial visual presentation (RSVP) from user-specific neural brain signals. The system comprises one or more processors and a memory having instructions such that when the instructions are executed, the one or more processors perform operations of extracting a set of image features from a pair of images in a rapid serial visual presentation (RSVP) image set. A predicted similarity metric is computed for the pair of images using the set of image features to detect at least one similarity in the pair of images, wherein predicted similarity metrics are computed to all pairs of images in the RSVP image set. The images in the RSVP image set are sequenced according to the predicted similarity metrics, resulting in a sequenced set of images. The sequenced set of images is then presented, and the system receives neural brain signals during visualization of the sequenced set of images to detect a P300 signal. A neural score is computed for each image in the sequenced set of images based on the existence and strength of the P300 signal, wherein the neural score represents a dissimilarity between at least two images in the RSVP image set. Thereafter, the system is optimized through a predictive model, which models the neural scores computed for the sequenced set of images. The images in the RSVP image set are resequenced according to the predictive model, and the resequenced images are presented. Finally, an image sequence prediction which minimizes a false P300 signal is output.

In another aspect, a sequence of non-target images is generated for presentation. The system receives the neural brain signals during visualization of the sequence of non-target images to detect a P300 signal, wherein the sequence of non-target images is used to eliminate a false P300 signal from the neural brain signals.

In another aspect, the system is further configured to determine the predicted similarity metric between images based on a weighted combination of a set of distance metrics, In another aspect, the system is further configured to adjust a weighting vector of the predictive model, such that a difference metric between the predicted similarity metric and the neural score is minimized for each consecutive image pairing in the RSVP image set.

The present invention also comprises one or more processors configured to perform operations of first dividing an input image into a plurality of image chips, then computing a set of motion channel feature maps from the image chips. A set of motion channels surprise maps is computed from the set of motion channel feature maps, and the image chips are labeled as static or moving. The system then prepares rapid serial visual presentation (RSVP) datasets of the image chips. The prepared RSVP datasets are presented for visualization and recording of neural brain signals. Additionally, an electroencephalography (EEG) score is computed from the neural brain signals based on a response to the image chips in the RSVP datasets. Finally, each image chip is classified as containing an item of interest or not containing an item of interest based on the EEG score.

In another aspect, the system is configured to create at least one video clip by taking an image chip labeled as moving from a set of multiple consecutive image frames. All video clips are collected into a RSVP video dataset.

In another aspect, the system is configured to record a neural brain signal upon an onset of presentation of each static image or video clip. An EEG data segment is then created from the neural brain signal, wherein the EEG data segment is a neural signature of a desired visual response for presentation of the static image or the video clip. The data segment is classified as a data segment containing an item of interest or a data segment not containing an item of interest.

In another aspect, the system is configured to receive a set of known images of targets and a set of known images of non-targets for training. The system then learns a classifier in a set of data segments corresponding to the set of known images of targets and the set of known images of non-targets, wherein two distinct classifiers are learned for a static type RSVP dataset and a video type RSVP dataset. The two distinct classifiers are employed to determine an EEG score for each type of RSVP dataset presentation.

As can be appreciated by one in the art, the present invention also comprises a method for causing a processor to perform the operations described herein.

As can be appreciated by one in the art, the present invention also comprises a computer program product comprising computer-readable instruction means stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
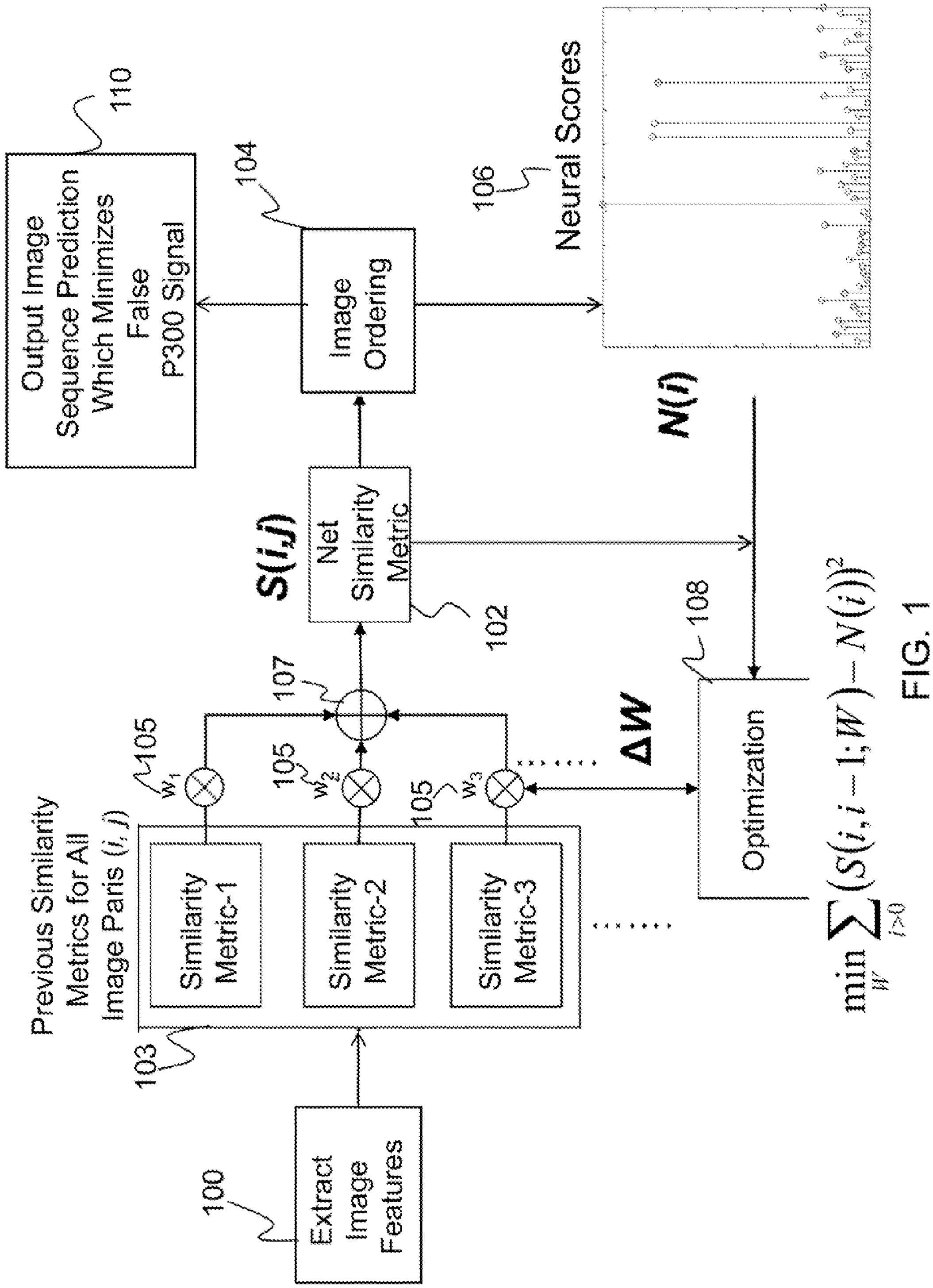
FIG. 1 is a flow diagram depicting an electroencephalograph (EEG)-assisted automated image ordering system according to the present invention.

The present invention relates to an anomaly detection system and, more particularly, to a system for detecting anomalies in a series of images by optimizing rapid serial visual presentation (RSVP) from user-specific neural brain signals. The following description is presented to enable one of ordinary skill in the art to make and use the invention and to incorporate it in the context of particular applications. Various modifications, as well as a variety of uses, in different applications will be readily apparent to those skilled in the art, and the general principles defined herein may be applied to a wide range of embodiments. Thus, the present invention is not intended to be limited to the embodiments presented, but is to be accorded with the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation, (1) Principal Aspects The present invention has three "principal" aspects. The first is a system for optimizing RSVP from user-specific neural brain signals. The system is typically in the form of a computer system, computer component, or computer network operating software or in the form of a "hard-coded" instruction set. This system may take a variety of forms with a variety of hardware devices and may include computer networks, handheld computing devices, cellular networks, satellite networks, and other communication devices. As can be appreciated by one skilled in the art, this system may be incorporated into a wide variety of devices that provide different functionalities. The second principal aspect is a method for optimizing RSVP from user-specific neural brain signals, typically in the form of software, operated using a data processing system (computer or computer network). The third principal aspect is a computer program product. The computer program product generally represents computer-readable instruction means (instructions) stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories.

The term "instruction means" as used with respect to this invention generally indicates a set of operations to be performed on a computer, and may represent pieces of a whole program or individual, separable, software modules. Non-limiting examples of "instruction means" include computer program code (source or object code) and "hard-coded" electronics (i.e. computer operations coded into a computer chip). The "instruction means" may be stored in the memory of a computer or on a non-transitory computer-readable medium such as a floppy disk, a CD-ROM, and a flash drive.

(2) Specific Details (2.1) Optimal RSVP Image Ordering Via Automated Learning from User-Specific Neural Brain Signals The present invention describes a system for ordering image subsets (called "chips") into sequences that maximize the likelihood of true "target" detection while simultaneously minimizing the likelihood of false alarms and unintended subject response while employing a RSVP protocol for an EEG experiment. As described above, RSVP measures the brain activity of a human subject while watching a stream of rapid images in order to find incongruities and inconsistencies in the images (i.e., "targets"). Image transitions of high contrast can induce false alarm signals in the subject's brain, reducing the effectiveness of the experiment.

In practice, using RSVP to analyze ground-based images presents a number of hazards that can cause the subject to exhibit a P300 neural signal without viewing a target. The P300 neural signal is a specific brainwave which occurs at a specific and fixed time delay from the presentation of the image. The P300 signal is far more reliable than voluntary responses of subjects, such as button presses, which exhibit variable delays. The P300 signal occurs as the result of "surprise", which can be the result of seeing a target in an image. Significantly, the P300 signal also can occur from the rapid exposure to images that have a high contrast to one another, such as an image of the dark ground followed by an image of the bright sky. The chips that are perceived as non-targets are considered "boring" and do not exhibit a P300 wave in the subject's EEG. Therefore, the presence of the P300 signal is a valuable discriminator between what the subject considers a "surprising" versus a "boring" chip.

The concept of "targets versus non-targets" can be extended to the concept of finding "items of interest" (IOI) among background items as described in U.S. patent application Ser. No. 12/316,779, entitled, "Cognitive-Neural Method for Image Analysis" (hereinafter referred to as the '779 application), which is hereby incorporated by reference as though fully set forth herein. These items of interest are generally objects, groups of objects, or spatial patterns in images and video and are of interest to the observer; they are generally application specific. For example, an image analyst looking for a helipad in wide-area satellite imagery will consider the helipad to be the "target" or "item of interest". However, a different analyst looking for a convoy of moving vehicles in the same satellite imagery will consider such a spatio-temporal pattern to be the IOI for that particular application.

The P300 signal occurs prior to the activation of the higher-level processes in the brain that identify and classify the target, but this is not a "subliminal" process. The subject generally realizes that a target was viewed, but does so much slower than the brain produces a P300 signal. The RSVP method capitalizes upon the inherent efficiency of these lower-level responses in the subject's brain. Research has shown that even at the high frequencies used in RSVP, the human brain performs admirably well at differentiating between "target" and "nontarget" images, and is far more efficient than if the subject had manually inspected and sorted the chips, as described by the Thorpe reference and the Gerson reference. RSVP has been used for a variety of applications, particularly those in which the subject is instructed to find targets in a sparse environment. For example, the subject might be instructed to look for buildings in satellite imagery from a desert.

As one might expect, measuring an involuntary response from a human brain poses a number of difficulties that must be addressed. In particular, the RSVP method does not specifically classify chips into target and non-target bins. Rather, chips are sorted into "boring" and "surprising" bins based on the presence of the P300 signal, and "surprising" and "target" classifications are not mutually exclusive. The typical experimental procedure for an RSVP session involves randomizing the sequence of chips. If the sequence contains a series of high contrast chips or chips whose features are very different from one another, an experiment can invoke a false P300 signal from non-target images based on "jarring" the visual field between dissimilar images.

For example, a ground-based scene might contain sky, background, foreground, and middle ground, each of which exhibit dramatically different colors, lighting, scales, and textures. A chip sequence consisting of a number of foreground chips followed by a single chip from the sky could easily produce a P300 signal based on the surprise generated by rapidly shifting from one set of image features to another in succession. Such false signals can mask the surprise produced by actual targets and increases the rate of false alarm. The system proposed in the present invention seeks to minimize this “jarring” effect by placing similar images next to one another in the RSVP queue, eliminating the effect of image jarring.

Furthermore, the present invention describes a method that combines image distance metrics and automated sequencing with EEG measurements of surprise to order image chips such that the occurrence of a false P300 signal due to image “jarring” is minimized. Such a method would be immensely useful for the reduction of false alarm rate for RSVP experiments. The present invention is applicable to IOI that include objects, groups of objects, and spatio-temporal patterns and events.

Current methods exist to sequence images according to their similarity, as described above. These algorithms create generally smooth sequences that contain a handful of bad transitions that can derail an RSVP experiment, which requires precision in the image ordering. The present invention overcomes the limitations of completely automated image sequencing by incorporating user feedback, which allows the system to learn which image transitions are most natural to the viewer and adjust the algorithms appropriately to emulate the human response.

Unlike previous attempts to find the optimal ordering of images for RSVP, the system described herein addresses the two major types of error in an RSVP experiment. A type I error, commonly called a false alarm, occurs when two contrasting non-target images are placed in immediate succession to one another. Type II errors occur when a target appears in the sequence that is not picked up by the EEG. This can occur when two target chips occur close to one another in the sequence, and the first one “shadows” the second, reducing the surprise that it incites. Finally, the problem of computing a sequence of images whose distances from one another are minimized is an analog to the “travelling salesman” problem. This problem is computationally intractable and cannot be solved absolutely without testing every possible image sequence, which is a complex and time-consuming process. The present system employs an effective heuristic method for quickly solving this problem without increasing the potential for inaccurate results. As can be appreciated by one skilled in the art, other heuristics exist to solve the traveling salesman problem and can be used.

U.S. patent application Ser. No. 12/653,561, entitled, “Image Ordering System Optimized Via User Feedback” (hereinafter referred to as the ’561 application) describes a system that can learn to put images in the optimal order based on learning from the user’s manual feedback. The ’561 application is hereby incorporated by reference as though fully set forth herein. In contrast, the system described herein can run independently of the user’s manual feedback, and instead automatically uses the EEG signal and prior knowledge of the “ground truth” (i.e., whether a chip is a target or non-target) during a training session to build a model of the ordering operation, that can be employed in field/testing operation, which will be described in further detail below. The present invention uses the user-specific EEG brain signals as an automated “teacher” and the system ordering algorithm as a “learner” such that after a few iterations of learning from the teacher, the system ordering algorithm can generate an optimal image order which matches what a specific user prefers. The system does not require motor or subjective response and, hence, can be much faster.

Unlike the prior invention described in the ’561 application that used the responses of the user, the current invention optimizes the image sequence based directly on the EEG signal. This ensures that the number of false positives in the EEG signal is minimized. The system then employs the fusion of various image metrics to emulate the human’s sequencing ability for groups of image chips, which are subsequently used in RSVP trials. The present invention accomplishes this by combining various perceptual and bio-inspired image features and their similarity metrics in order to create a sequence that minimizes this image jarring effect to the viewer. The image sequence is presented to the user and his/her EEG signals are then analyzed and used as a “teaching” signal. The system uses this teaching signal and learns to adjust the weighting parameters among the different image distance (similarity) metrics. Based on the new weighting, a new sequence is computed and presented to the user. The cycle continues until the algorithm is able to accurately emulate the sequencing ability of the subject. This can be readily extended to multiple image sets and multiple users as well.

The invention described herein is useful for any application that employs the RSVP method for optimal sequencing for rapid object classification. For example, it can be employed in human-assisted threat assessment and threat queuing application in which the system must scan a wide field-of-view and report any anomalies to the landscape. In these instances, automated classification methods might fail. Other non-limiting examples of potential applications include automotive safety, factory safety and efficiency (e.g., sorting tasks), intelligence analysis, and surveillance.

A flow diagram depicting the image ordering system in the present invention is illustrated in FIG. 1. As shown, the system consists of five stages, which extract the image features 100, compute the distance metrics (net similarity metric 102) from a series of similarity metrics 103, sequence the images (image ordering 104), obtain EEG signals from the user, compute neural scores 106 from the EEG signals, and then optimize (optimization 108) the sequence to minimize the false alarm rate.

The EEG signals, which are processed into neural scores 106, are used as a “teacher”, and the system learns optimal weightings from the EEG signals to determine optimal image ordering. After a few iterations and a convergence criteria, the system ordering of images can become stand-alone, since the system has effectively learned automatically from user-specific brain neural signals. The set of stages is repeated until the system is able to predict an image sequence that does not cause false P300 signals (output image sequence prediction which does not cause false P300 signal 110) in EEG during RSVP. Each of these stages is described in detail below.

(2.1.1) Extract Image Features

Many different image features and combinations have been used in image similarity and search problems. Color retrieval usually yields the best results, in that the computer results of color similarity are similar to those derived by a human visual system as described in the Rogowitz reference. Other features include texture, shape, edges, bio-inspired features, etc.

For color features, images are typically read as RGB models and then transformed into the HSV color model. The RGB color model is composed of the primary colors red, green, and blue. They are considered the “additive primaries” since the colors are added together to produce the desired color. The HSV color model, as described in the Robowitz reference, was used in the present invention. The HSV color model defines colors in terms of three constituent components: hue, saturation, and value. The hue and saturation components are intimately related to the way the human eye perceives color, because they capture the whole spectrum of colors. The value represents intensity of a color, which is decoupled from the color information in the represented image.

Based on prior art in the domain of color features for image similarity problems as well as experimental tests, the decision to use a small group of local and global color features as the basis set of image features in this embodiment was made. These image features can be extended to include other types of image features just as easily. However, experimental tests indicated that the gradient of HSV gave better image ordering results and, thus, the HSV model was selected.

The first step in preparing the image is to compute the HSV colors from RGB, (i.e., $I_{RGB} \rightarrow I_{HSV}$). Once $I_{HSV}$ is computed, the Gradient $G(I_{HSV})$ is then computed as follows:

$$G(I_{HSV}) = \begin{matrix} \partial_x I_H & \partial_y I_H \\ \partial_x I_S & \partial_y I_S \\ \partial_x I_V & \partial_y I_V \end{matrix},$$

where $I_H$, $I_S$, and $I_V$ represent the raw values for the hue, saturation, and value in the image, respectively, and $\partial_\chi$, $\partial_y$ represent the gradient in the image along the x and y axis, respectively. The second image features extracted are the image histograms for each of the I, S, and V channels denoted as $H(I_H)$, $H(I_S)$, and $H(I_V)$, respectively. Each histogram is normalized to sum to one.

(2.1.2) Similarity Metrics

To compute the similarity between a pair of images i and j, the image features from the first step are used to compute several "distance" (or similarity) metrics 103, as shown in FIG. 1 When the metrics are small (i.e., close to 0), the images are more similar to each other, and vice versa.

The "gradient" distance metric $K_G$ uses the L1 norm of the gradient difference between the images and is calculated as follows:

$$K_G(i,j)=\Sigma|G(i_{HSV})-G(j_{HSV})|.$$

Note that in the above equation, i and j represent images in HSV color space. The goal of this operation is to capture local common structure in images i and j.

The "histogram" distance metric $K_{HT}$ uses the L1-norm of the histogram difference between the images as follows:

$$K_{HT}(i,j)=\Sigma_{H,S,V}|H(i)-H(j)|.$$

The histogram differences are used to allow the eventual summed distance measure to not be overly sensitive to noise in images.

Another image distance metric used is the diffusion distance, a histogram distance measure described by Ling et al. in "Diffusion Distance for Histogram Comparison" in *Institute of Electrical and Electronics Engineers* (*IEEE*) *Computer Society Conference on Computer Vision and Pattern Recognition* (*CVPR*), 2006 (hereinafter referred to as the Ling reference), which is hereby incorporated by reference as though fully set forth herein. For two histograms $h_1$ and $h_2$, the diffusion distance is computed as:

$$K(h_1, h_2) = \sum_{l=0}^{L} |d_l(x)|,$$

where $d_1$ is computed recursively as below:

$$d_0(\chi)=h_1(\chi)-h_2(\chi)$$

$$d_1(\chi)=[d_{l-1}(\chi)*\Phi(\chi,\sigma)]\downarrow_2.$$

$\Phi(\chi, \sigma)$ is a Gaussian filter, with the tunable parameter $\sigma$ to describe how much each layer diffuses. The symbol $\downarrow_2$ represents the down sampling of the histograms, and L is the number of layers of diffusion, as described in the Ling reference.

The "diffusion" distance metrics $K_H$, $K_S$, and $K_V$ between the images i and j for each image channel (H, S, and V) histogram are computed as:

$$K_H(i,j)=K(H(i_H),H(j_H))$$

$$K_H(i,j)=K(H(i_S),H(j_S))$$

$$K_H(i,j)=K(H(i_V),H(j_V)).$$

The predicted similarity metric, S, between images i and j is a weighted combination of the above five metrics, given below:

$$S(i, j; W) = \sum_{m \in G,HT,H,S,V} \{W_m K_M(i, j)\} = W_G K_G(i, j) + W_{HT} K_{HT}(i, j) + W_H K_H(i, j) + W_S K_S + W_V K_V(i, j).$$

This is the weighted sum of the channels over the color space that employs the weighting vector, W. As illustrated in FIG. 1, each predicted similarity metric is expressed as a function of its respective weighting vector 105, and the weighting vectors 105 are then added 107 to achieve the net similarity metric 102. The weights have a profound effect on the similarity scores and will be optimized at a later time. Note that the predicted similarity metric S can be extended for arbitrarily weighted image metrics for ordering. Additionally, through normalizing the data, a metric distance measure is achieved. In other words, the metric satisfies the triangle inequality. The above predicted similarity metric is computed for all image pairings in the RSVP image set. For N images, there are $N_{C_2}/2$ distinct image pairs. The above K-metric is computed for each of those pairs, where $N_{C_2}/2$ represents the choose function of N and 2 (N choose 2) divided by 2 (since image pairs 1, 2 and 2, 1, for example, would be considered the same pair) to get the number of unique image pairs.

(2.1.3) Clustering and Image Ordering

The problem of ordering the images according to their distances from one another reduces to the same problem as the Traveling Salesman Problem (TSP). The TSP works on a graph G=(V, E), where V is a set of vertices (often cities, locations), and E is a set of edges between the vertices. Each $e \in E$ has a weight $W_i$. The goal of the TSP is to find a tour of edges $T \subseteq E$ such that all vertices are visited only once and the following is minimized:

$$\sum_{i \in T} w_i.$$

Ordering a set of n images consists of solving TSP on $K_n$ and completing the graph with n vertices, where $K_n$ is the difference metric that is then weighted. The weights $W_i$ are the distances between the endpoints of the edge $W_i$.

Content-based image retrieval (CBIR) systems routinely use multi-dimensional scaling (MDS) and hierarchical clustering for the visualization of both stored and retrieved images. Various structures have been developed based on Euclidean distance metrics, such as the k-d trees and the R-d trees and its variants. Since the goal is to rapidly order images for presentation and TSP is known to be NP-Complete, an approximation was chosen to solve the TSP problem, as applicable to the image ordering problem described in the present application. Another reason for selecting an approximation over the exact answer is that the images are presented to the user and need to be ordered from a user perspective. It cannot be guaranteed that the optimal mathematical ordering is the most visual appealing. What is obtained in the ordering is a great starting point from which the user can improve through a few trials. The algorithm used to approximate the TSP is described below and guarantees the following:

$$\sum_{i \in T} w_i \leq 20PT,$$

where OPT is the optimal value as described by Vazirani in *Approximation Algorithms*, Springer-Verlag, Berlin, Germany. p. 32, 2004 (hereinafter referred to as the Vazirani reference), which is hereby incorporated by reference as thought fully set forth herein. The algorithm used is only valid for metric TSP, which will still work in the present case since the distance measure is a metric. The main steps in this algorithm are to first construct a minimum spanning tree. Then, every edge is doubled to form an Euler Graph. The next step is to build an Euler path in the minimum spanning tree. The Euler path is then repaired to be a Hamiltonian by trying to walk along the path and skip over all elements already visited. A Hamiltonian path visits every vertex once and only once. An Euler path may have traversed a vertex more than once, and the repair process removes these vertices that may have been traversed more than once, thus making it Hamiltonian. The results of the above image ordering algorithm is an ordered set of images denoted by $o_A$. This ordered set of images is presented to the user for visual inspection and potential re-ordering (i.e., the user can click and drag any image and move it to a different position in the order).

(2.1.4) Data Collection Using EEG

The next step accomplished by the system is to generate a sequence of non-target (i.e., distracter) images and display them in a RSVP method measuring the subject's EEG to detect P300 signals. This will act as a "ground truth" for the image ordering algorithm, since the purpose is to eliminate false P300 signals from the subject's EEG.

Figure 2:
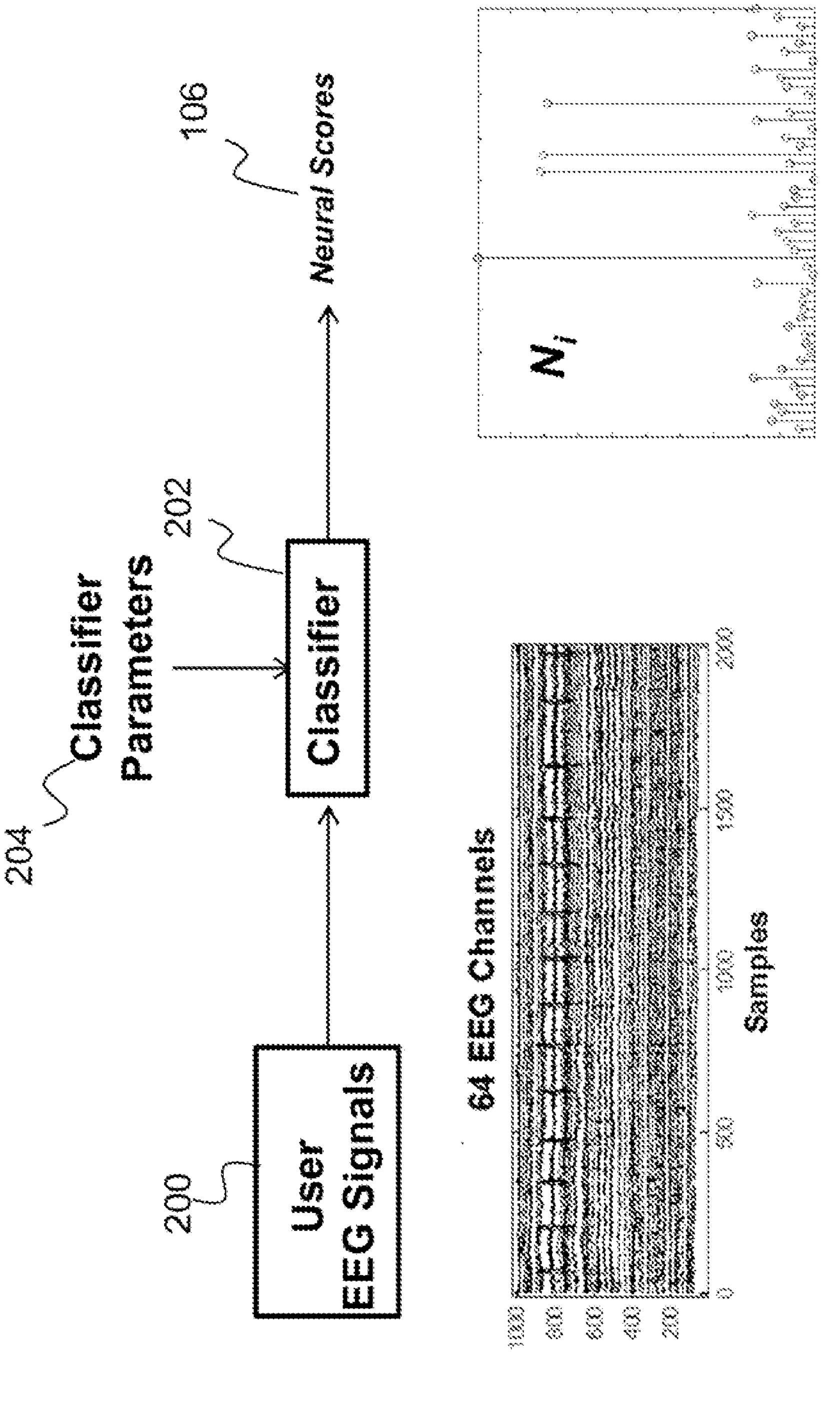
FIG. 2 is a flow diagram depicting a method for computing a neural score for each image transition according to the present invention.

The method for computing neural scores from the user's EEG signals is illustrated in FIG. 2. The user's EEG signals 200, which are very noisy, are processed by a trained classifier 202 (trained by classifier parameters 204), and each image transition is given a neural score 106 between zero and one based on the surprise that the transition caused. Classifier parameters could consist of weights estimated for the time samples of EEG channels. One non-limiting example is the weights for a multilayer perceptron as described in the Gerson reference. Additionally, object recognition in vision classifiers could be used. Ideally, in a sequence with no targets, the neural scores 106 will all be equal to zero. A base sequence of non-target images is generated using the predictive (semi-optimal/greedy) metric. In this instance, images next to each other should be mostly similar to one another. The ordered images are then presented in an RSVP sequence, and the user's EEG signals 200 are measured to detect P300 signals.

For each image chip, a target score between zero and one is computed based on the existence and strength of a P300 signal (i.e., the surprise that the image transition caused). This score is called the neural score 106, N(i). The neural score 106 is representative of the dissimilarity between an image, i, and the one displayed before it. Ideally, this score should be zero, since there are no targets in the sequence. A high neural score indicates image jarring that must be rectified by adjusting the image order. It should be noted that unlike the previous step where all possible image pairings are considered, the EEG similarity scores only consider image pairings where j immediately follows i (i.e., j=i+1). This is done using an optimization step, as described in detail below. Note that this is only true for this specific embodiment. As can be appreciated by one skilled in the art, it would be straightforward in another embodiment to have the neural score 106 be reflective of dissimilarity with a number of previous images or to use a fading memory model where the weights reduce as the distance of the previous frame from the current frame increases.

(2.1.5) Optimization

The final step that the system employs is an optimization step, where the purpose is to adjust the weights of the system such that the system predicted order closely mirrors the optimal EEG determined order. The objective in this case is to adjust the weights of the predictive model such that it matches (and will eventually predict) the neural scores produced by the EEG. If the system can adequately model how the subject's brain will respond to a given set of images, it can then arrange them in such a manner as to minimize the jarring effects caused by the image transitions.

The optimization ($W_{opt}$) is carried out by adjusting the weighting vector, W, of a predictive model such that a difference metric between the system predicted similarity metric, S, and the neural score, N, is minimized for all consecutive pairings in the sequence according to the following:

$$W_{opt} = \operatorname*{argmin}_{W} \sum_{i>0} (S(i, i-1; W) - N(i))^2.$$

In a desired aspect, a squared difference is used but other distance metrics for minimization, such as non-Euclidean/error terms, are also possible.

It should be noted that while the predicted similarity metric, S, is defined on all image pair combinations of i and j, the neural score is only defined on pairings of consecutive images in the RSVP sequence. Therefore, the only predicted similarity scores employed in this optimization are those for the current frame, i, and the previous frame, i–1. This is a non-limiting example of a possible cost function to reduce the distance between the predicted model and neural scores. Since this is a general inference problem, other methods such as maximum likelihood estimation (MLE) are also acceptable alternatives to this expression.

(2.1.6) Re-Sequencing and Iteration

Once the weights have been computed that cause the predicted model to agree closely with the neural scores, the images are reordered according to the new weights into a new sequence. This sequence is then run through the EEG classifier again and new neural scores are computed. One can run this cycle as many times as is necessary to find agreement between the predicted similarity and the neural response. Such an agreement might be a given number of iterations, the difference between the metrics falling below a given threshold, or any other stopping condition that the user chooses.

To summarize, this image ordering system executes the following sequence of commands. First, using a nominal set of weights, the predictive model is used to generate an ordered image sequence. Next, similarity scores, $S_{ij}$, are computed for each image transition. The sequence is then displayed via RSVP to the subject, and the resulting EEG signal is monitored. From the EEG signal, a neural score, $N_i$ is computed. The weights are optimized such that the difference between S and N is minimized. The images in the sequence are then reordered. The process then returns to the second step of displaying the sequence via RSVP to the subject and continues until some stopping condition is met. As a non-limiting example, a value of 0.01 was chosen.

(2.2) Optimized Static and Video EEG RSVP Method Based on Motion Surprise Computation The present invention also describes a system for optimizing search and detection performance for items of interest (IOI) in large-sized images and videos that uses a RSVP-based EEG process for computing the optimal presentation sequence. As described above, an IOI could be a single object, group of objects, specific image regions, specific spatio-temporal pattern/sequence or even the category that the image itself belongs to (e.g., target or non-target).

The invention works by first computing a motion surprise map on image sub-regions (chips) of incoming sensor video data and then using the motion surprise maps to label the chips as static or moving. It then uses a static or video RSVP presentation and decoding algorithm, depending on the whether the chip is static or moving, respectively, to optimize EEG based detection of IOI in each chip, thus providing IOI detections for the entire incoming dataset.

The invention described herein is useful for any application that employs the RSVP method for using neural signatures to aid object detection and classification. For example, it can be employed in human-assisted threat assessment and threat queuing applications in which the system must scan a wide field of view and report any anomalies to the landscape. In these instances, automated classification methods might fail. Additionally, it can be employed for search and rescue operations or in surveillance applications where any activity is an unexpected occurrence, such as in a desert or mountain range or on the open sea. It is particularly useful in applications where size, weight, and power are at a premium. Furthermore, the system can be used as a front-end for any application that employs visual object recognition and scene understanding to extract regions of interest for identification. Other non-limiting examples of potential applications include automotive safety, factory safety and efficiency (e.g., sorting tasks), intelligence analysis, and surveillance. Any application that is specifically looking for static or moving IOI only can also benefit from this invention.

The present invention builds upon and extends works on previous inventions including U.S. patent application Ser. No. 12/214,259, entitled, "Visual attention and segmentation system" (hereinafter referred to as the '259 application), which is hereby incorporated by reference as though fully set forth herein. The invention described is also related to the '779 application and the '561 application described above.

The present system employs two distinct classifiers (i.e., static or video RSVP-based EEG) that are triggered based on the amount of motion surprise in a chip, as opposed to just raw motion that is susceptible to false alarms. In addition, the simplicity of the algorithms presented herein allow the system to compute results in real-time and allow it to be easily implemented in a hardware system for even faster processing with low power consumption. The present system and method can be used as a front-end to a larger system that includes object recognition and scene understanding modules that are cued by the detected IOI.

In the '779 application, the attention (saliency) algorithm detects initial candidates for IOI followed by static RSVP presentation and neural or EEG decoding. While this approach works well, it uses exactly the same algorithms for any type of IOI (static or video). In many real-world applications, moving IOI are of greater importance (e.g., a dismount or vehicle moving in desert or mountain terrain). The present invention is based on the premise that detection performance will be improved by first detecting motion surprise and then using a static- or moving-tuned EEG classifier approach for neural detection. The system presented herein improves upon moving IOI detection and, in the process, improves static IOI detection as well. It uses a RSVP presentation and decoding method tuned to whether the IOI is static or moving via separate static and video EEG classifiers. The motion detection modifies the previous attention algorithm described in the '259 application and applies only a small additional calculation to the base attention algorithm. This simplicity allows it to be mapped to hardware that conforms to low size, weight, and power constraints.

The '779 application described a method and system for intelligent and rapid search and categorization of IOI in imagery and video. These IOI could be a single object, group of objects, specific regions, specific spatio-temporal pattern/sequence or even the category that the image itself belongs to (e.g., target or non-target). The '779 application was based on combining the following two key algorithms. The first is the cognitive algorithm that employs a feature-based approach, which computes attention by constructing a saliency map from a set of biologically inspired features extracted from the image. The cognitive algorithm performs initial IOI extraction automatically using saliency. The second algorithm is the neural algorithm, which is based on neural signatures of target detection. The neural algorithm in the '779 application uses batch mode neural signatures of target detection using RSVP EEG processing of static images to produce validated IOI. Additionally, there is a third and optional adaptation algorithm that uses automated or manual cues (e.g., validated regions, user input, categorization) to perform learning to bias future attention processing. Thus, an adaptation module provides dynamic, on-line learning capability for new IOIs.

The present invention can be used as a stand-alone module for identifying important regions of dynamic visual imagery (i.e., video) where object identification is not critical to the task, or as part of a larger vision system that includes modules for object classification and identification subsequent to surprise map generation. Non-limiting examples of these applications include automatic surveillance systems, intelligent image analysis, search and rescue, embodied robots, and detection of obstacles by an unmanned vehicle. The surprise algorithms that this invention employs are inspired by findings in human visual psychophysics and primate neurophysiology.

Figure 3:
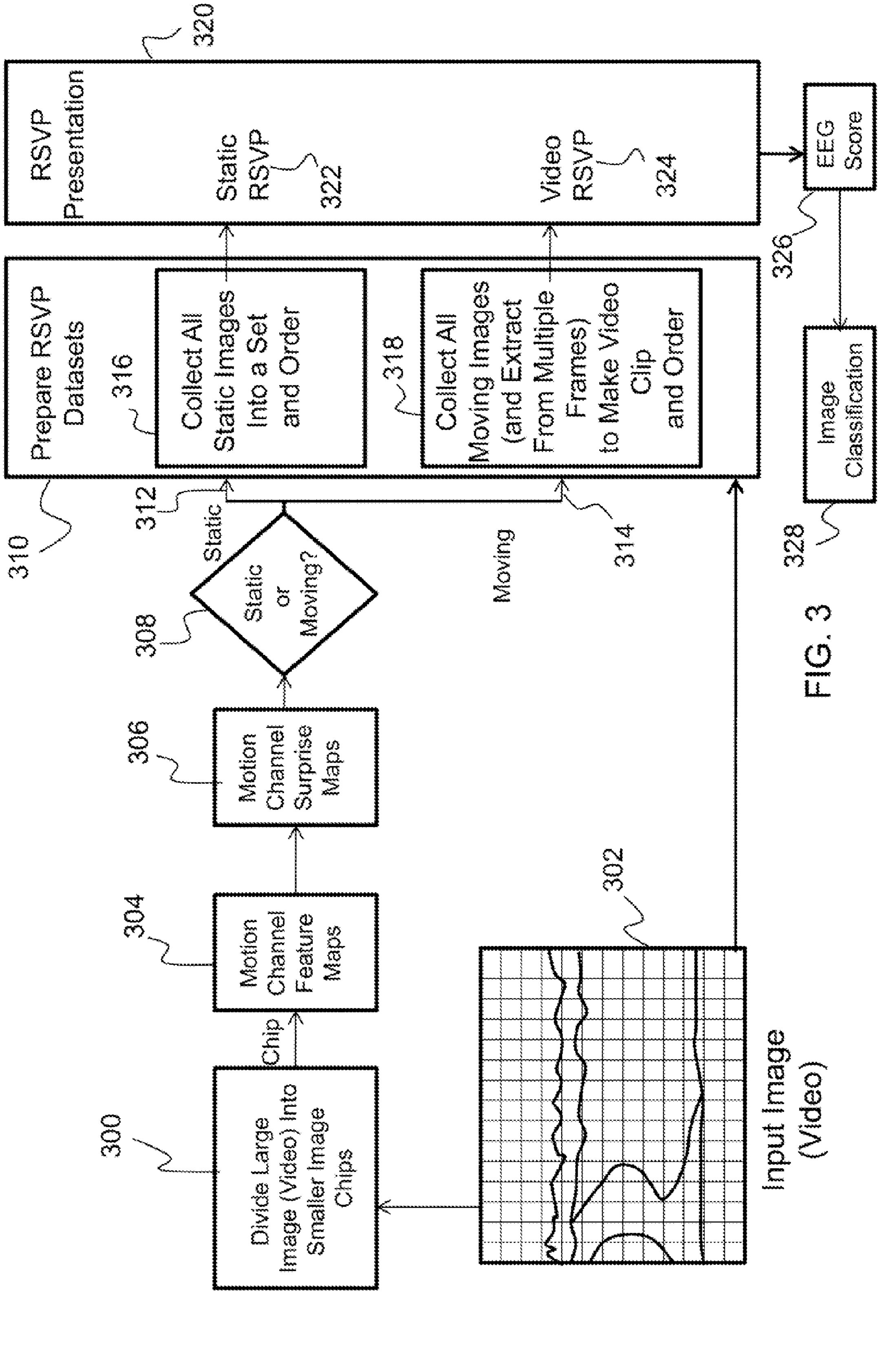
FIG. 3 is a flow diagram depicting a system for optimized static and video EEG rapid serial visual presentation (RSVP) based on motion surprise computation according to the present invention.

A flow diagram for the method and system described herein is illustrated in FIG. 3. The system consists of seven modules, which will be described in detail below. In the first module 300, the system takes a frame (i.e., image) of an input image 302 (e.g., video from a high resolution camera) and divides the frame into a number of smaller image regions (henceforth referred to as chips). For example, a 2048×2048 pixel input frame can be divided into 8×8 pixels or 64 chips, each of size 256×256 pixels. The size of a chip is typically based on the RSVP method employed. In addition, since chips can be processed in parallel in the algorithmic stages, the processing capability of the software or hardware employed in these stages may also affect the chip size parameter. Based on prior art and previous work described in the '561 application, U.S. patent application Ser. No. 12/584,744 entitled, "Visual Attention System for Salient Regions in Imagery" (hereinafter referred to as the '744 application), and the domains of EEG RSVP and saliency/surprise algorithms as well as experimental tests, the 256×256 pixels chip size is used in the present embodiment. The chips are then presented as an input to a second module 304 of the system. The '744 application is hereby incorporated by reference as though fully set forth herein.

In the second module 304, motion channel feature maps are computed. As with the computation of the saliency algorithm described in the '259 application, the first step in the second module 304 is to compute a series of feature maps representing intensities and motion patterns from a series of consecutive static color images of a scene representative of continuous frames in a video. If the image sequence is in black and white, it is converted into a RGB format, where all three channels have the same value (retaining the black-and-white appearance) for feature map calculation. Furthermore, one must first compute a pair of intensity channels L and D (light and dark, respectively) which are calculated from the input image by averaging the red, green, and blue channels (r,g,b) as follows:

$$L=(r+g+b)/3$$

$$D=255-L.$$

Additionally, channels corresponding to motion in various directions are computed by differencing the intensity (L) maps of the current and previous frames at a slight directional offset. This is typically done for the four cardinal directions, up, down, left, and right, as well as once without any offset, which detects objects that move in place or appear to glimmer. While there are more input channels that one might conceive, this particular set represents the most basic required for adequate performance of the surprise algorithm. Center-surround color maps corresponding to the receptive fields in the retina for the motion channels (center and surround are from motion in the same direction) are computed from the input channels from the Difference of Gaussians (DoG) between an "ON" center feature and a contrasting "OFF" surround feature. Both the center and surround channels are convolved with a two-dimensional Gaussian kernel, where the surround kernel has a larger bandwidth than the center kernel. A feature map is computed when the surround channel is subtracted from the center channel. This process is repeated for each center-surround channel pairing for each of the motion directions as described in the '259 application. Each feature map is then normalized between zero and one. The resulting set of feature maps indicates anomalous regions along that particular feature within the still frame of the scene, and each frame in the video sequence generates its own series of feature maps.

Figure 4:
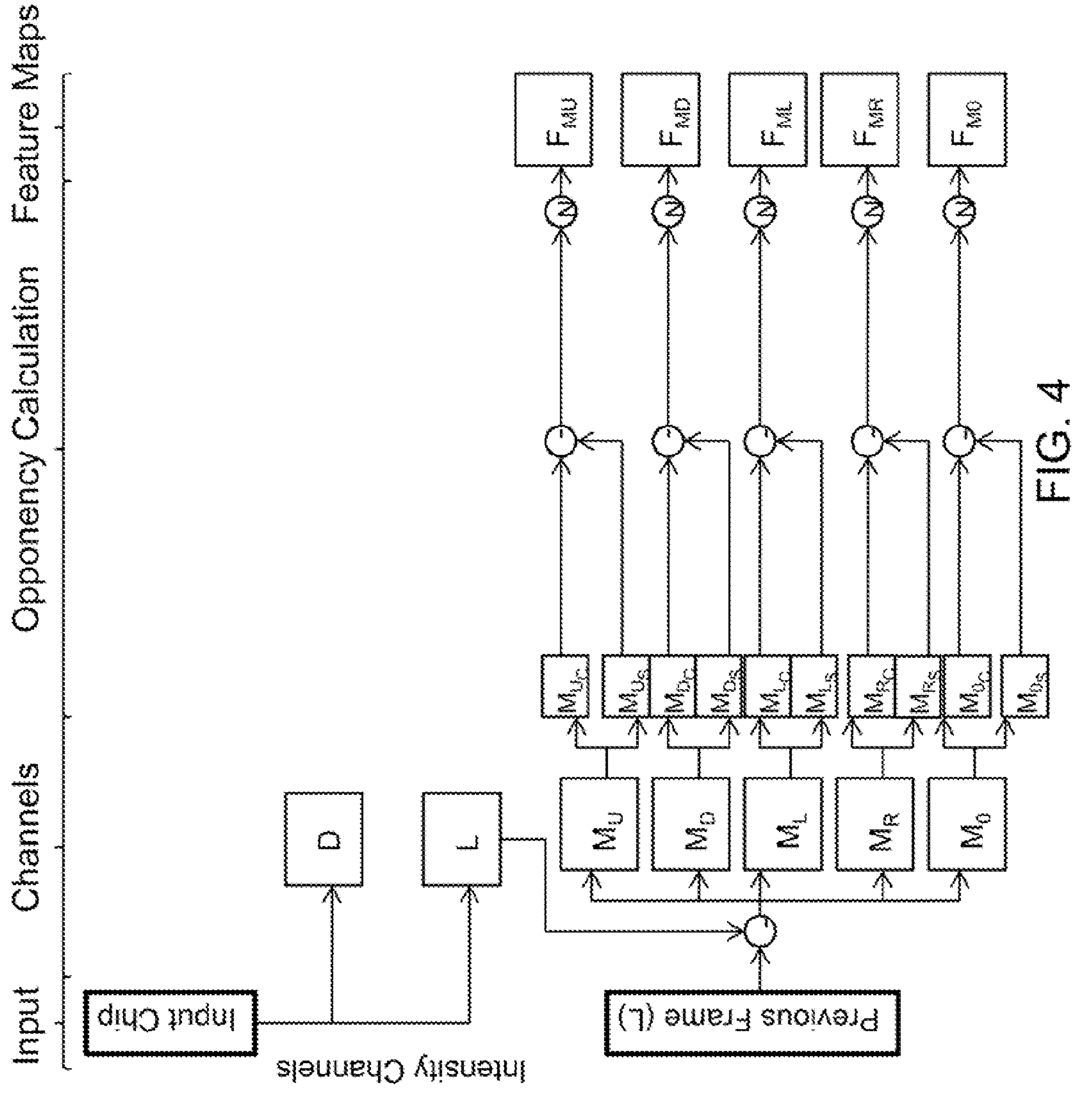
FIG. 4 is an illustration depicting an algorithm to compute motion channel feature maps according to the present invention.

FIG. 4 illustrates the algorithm used to compute the motion channel feature maps. In FIG. 4, $M_U$ denotes "motion channel up", $M_D$ represents "motion channel down", $M_L$ denotes "motion channel left", $M_R$ represents "motion channel right", and $M_O$ denotes "motion channel". $M_{U_C}$ denotes "motion channel up, center feature", $M_{U_S}$ represents "motion channel up, surround feature", $M_{D_C}$ denotes "motion channel down, center feature", $M_{D_S}$ denotes "motion channel down, surround feature", $M_{L_C}$ denotes "motion channel left, center feature", $M_{L_S}$ represents "motion channel left, surround feature", $M_{R_C}$ denotes "motion channel right, center feature", $M_{R_S}$ denotes "motion channel right, surround feature", $M_{O_C}$ represents "motion channel center feature", and $M_{OS}$ denotes "motion channel surround feature". $F_{MO}$ denotes "feature map", $F_{MU}$ denotes "feature map up", $F_{MD}$ represents "feature map down", $F_{ML}$ represents "feature map left", and $F_{MR}$ denotes "feature map right". Additionally, a circle with a + inside represents pixel by pixel rectified addition, and a circle with a – inside represents pixel by pixel rectified subtraction. N denotes normalization.

Referring to FIG. 3, the second module 304 computes feature maps that can be used as an input to a standard saliency or attention algorithm, such as described in the '259 application. However, there is a fundamental problem with using saliency to analyze complex dynamic imagery, such as natural scenes. A standard saliency algorithm run on a stream of input data will return the salient objects or events from that specific frame, only using other frames in a very limited way (e.g., to compute motion). Even then, the saliency algorithm will only use the previous frame to calculate dynamic features. There is no notion of continuity or memory across multiple frames and, consequently, the resulting saliency maps can be very noisy. For example, a forest scene in a slight breeze is likely to contain a lot of motion, and a saliency map will detect it all. However, all of this saliency can easily swamp the system and blind it to other, more anomalous, results, such as animals or vehicles of interest. Even if the target was a different color and clearly visible in the scene, it might be difficult to differentiate between the target's saliency and the ambient saliency of the scene using a standard saliency algorithm.

In contrast, the human visual system can "tune-out" repeatedly distracting features within a scene so as to be more sensitive to new and unexpected anomalies. Surprise algorithms are immune to this type of swamping and often provide better detection of anomalous events in detailed dynamic imagery than simple saliency algorithms as described by Itti and Baldi in "Bayesian Surprise Attracts Human Attention" in *Vision Research* 49: 1295-1306, 2008 (hereinafter referred to as the Itti and Baldi reference), which is hereby incorporated by reference as though fully set forth herein. This is because rather than processing single frames quasi-independently of one another to perform basic anomaly detection, surprise algorithms integrate the information provided by the saliency maps over multiple frames in order to differentiate between salient background "noise" events and events that are anomalous to the long-term structure of the scene.

Computationally, however, paying attention to a scene and extracting highly surprising locations or regions provides a great challenge. A robust vision system must be able to compute the saliency of regions of a scene, integrate the saliency at each spatial location over time, and determine what locations in a scene draw the most surprise so that they can be identified or interpreted. Because the surprise algorithm uses saliency but clearly improves upon its output by incorporating a notion of temporal integration, it should not be considered as a competitor to saliency, but rather as an extension of the saliency concept to the instance where input comes as continuous frames.

The present invention uses an algorithm that uses the motion feature maps from the second module and, with some additional calculations, computes motion surprise information in the third module. The third module first computes a baseline or "status quo" within the scene for motion features, so that the system can detect when an event occurs that disagrees with the historical distribution of these features within the scene. This is done by computing a "prior map," P, for each feature by integrating the sequence of feature maps over time. There are many possible ways to integrate the information from a temporal series of feature maps into a prior map, but the simplest process is through a weighted expected value (e.g., the mean), where more recent frames provide a stronger influence on the prior map than frames encountered long ago. For a given feature, this can be expressed for any spatial location (i,j) in the map as the following:

$$P_{i,j}(t)=\sum_{T=0}^{t} w_x F_{ij}(T)$$

where the decay of the weights is determined by some time constant. For example:

$$W_T=e^{-\alpha(t-T)}$$

with the constraint that all weights sum to 1:

$$\Sigma_\chi W_\chi=1,$$

where t is the current time, T is the time index (which goes from 0 to current time t), $F_{ij}$ is a feature map at spatial location i,j, and $\alpha$ is a decay term (chosen here to be 0.1).

This method requires the storage of t feature maps, which is generally not difficult as these maps are generally decimated from the original image. As new frames are processed, the new feature maps are integrated into the existing prior maps, ensuring that they always remain up-to-date with the most current features of the scene. This is particularly important if the system is meant to be run for a long period of time, where atmospheric and lighting conditions are likely to change over the course of the sequence. While there is no specified training period and the system can begin to generate surprise maps immediately after the system begins to process frames, it is generally a good idea to allow the prior map to stabilize before seriously considering the results.

Optionally, this system could employ different time scales for the weighting. For example one set of weights could use a time constant, $\alpha$, that is larger, and hence the weights decay more slowly, placing increased emphasis on older values, while a set of weights corresponding to a shorter time scale could be employed to emphasize more recent events. In other words, $\alpha$ can be large or small for the two sets of weights. For example, $\alpha$ could be 0.1 as the default value (small), as chosen, and could be 0.5 for the larger time constant causing slower decay. If this method is employed, then the prior map would be equal to some normalized combination of the maps from these two time scales.

Once the system has generated a relatively stable prior map, one can generate the surprise map in the third module. The first step is to compute the rectified difference between each feature map for the newest frame (at time t+1) and its corresponding prior map:

$$SFM_{ij}(t+1)=|P_{ij}(t)-F_{ij}(t+1)|.$$

Figure 5:
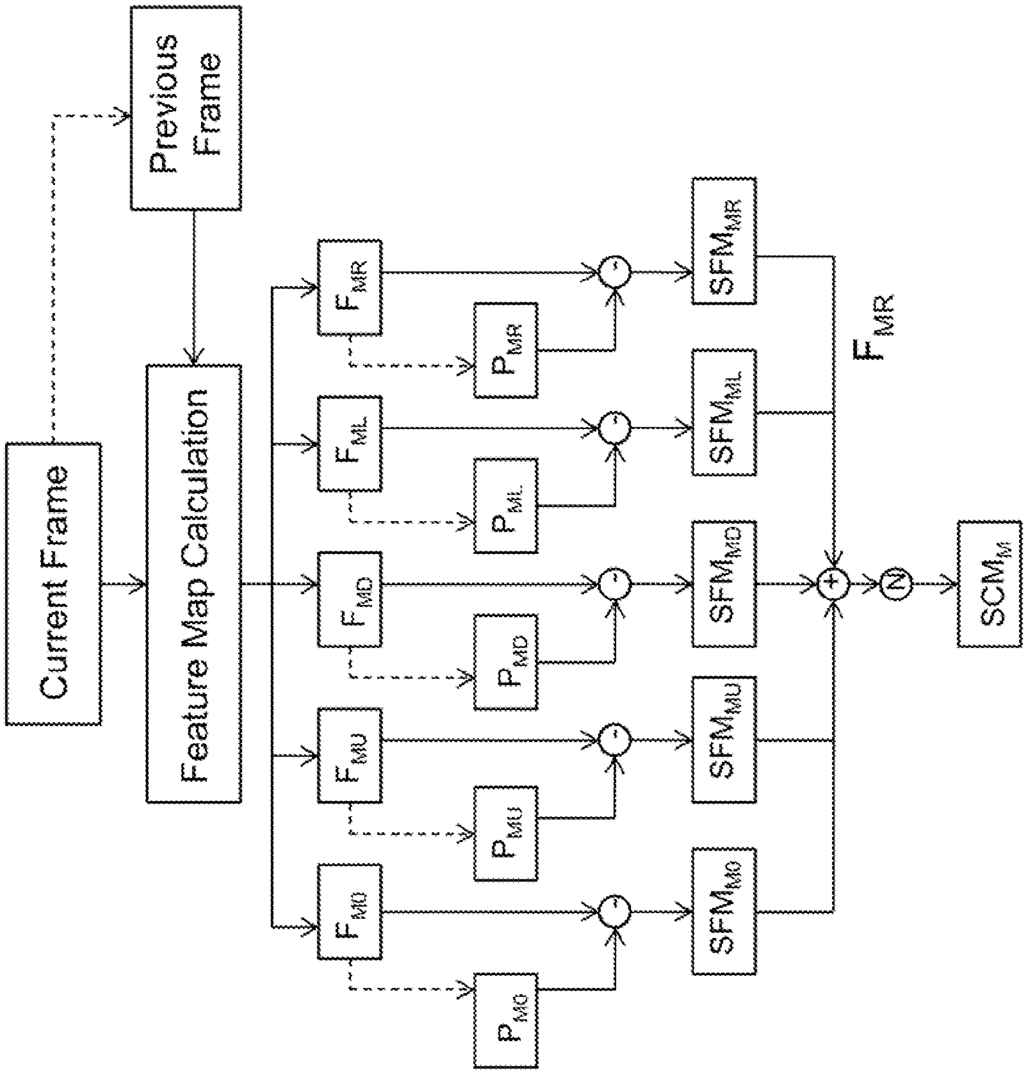
FIG. 5 is an illustration depicting an algorithm to compute a motion surprise map according to the present invention.

The resulting map provides a spatial map for each feature that shows how much the current scene deviates from the norm for that feature. These are known as surprise feature maps (SFMs) and are analogous to the feature maps in the generic saliency algorithm. The surprise feature maps that correspond to a given feature type are added and normalized to create surprise conspicuity maps (SCMs). Color SFMs are added together and normalized to create a color SCM, and motion SFMs combine to form a motion SCM, and so on. Finally, the SCMs are added together and normalized to create a surprise map. After surprise is computed for the frame, the feature maps are integrated into the appropriate prior maps, so that they are updated with the most recent information. FIG. 5 illustrates the algorithm to compute a motion surprise map of the third module (FIG. 3, 306). In FIG. 5, P represents "prior" and includes the same notations for MO, MU, MD, ML, and MR as FIG. 4 (e.g., $P_{MU}$ denotes "prior feature map up").

It should be noted that the aforementioned example assumes that the sensors on the system are cameras collecting video data. However, as can be appreciated by one skilled in the art, a similar surprise algorithm can be devised for any type of sensory input, and, therefore, this system can be applied to any type of sensor array. For the purpose of this invention, it is assumed that the surprise is computed in hardware as a black box, whose only inputs are the current frame of sensor data, the previous frame of sensor data (for dynamic feature computations), and the most recent set of prior maps, which are updated and returned by the hardware as each frame is processed. This level of abstraction maximizes the applicability of the system and reduces the need to cater to specific nuances of the surprise algorithm. In fact, the present invention does not depend on the specific implementation of the surprise algorithm apart from the memory structures that it stores.

In the fourth module (FIG. 3, 308), a determination is made regarding whether a chip is static or moving. In a desired aspect, simple metrics computed based on a surprise map (e.g., max. and mean) are used to determine a single surprise score and compare it with a threshold value (ad-hoc). If the surprise score exceeds the threshold, then the chip is labeled as moving. If the surprise score is below the threshold, then the chip will be labeled as static. In another aspect, an additional calibration (training) procedure is used where data with various (e.g., size, velocity) moving and static objects (e.g., dismount, vehicle) is collected at various ranges from a sensor. A surprise value is then computed to determine a threshold.

In the fifth module 310 of the system, the system prepares RSVP datasets. Preparing RSVP datasets for a static case 312 or a moving case 314 is generally similar. In a static case 312, it involves collecting all static images (chips) into a set and ordering them 316. The static images can be ordered according to the algorithms of the present invention (e.g., similarity metrics and user EEG optimization) or they can be randomized. In a moving case 314, it involves first creating short video clips by taking the same chip from multiple consecutive frames. Then, all the moving images (video clips) are collected and ordered 318 (i.e., optimized ordering or randomized). In other words, all images that are moving are first convened into a video clip by collecting data across multiple frames, and the set of video clips is ordered.

The sixth module 320 consists of RSVP presentation of static RSVP 322 or moving RSVP 324. In a desired aspect, visual images corresponding to the potential IOI regions tagged by the cognitive module are presented as RSVP images on a standard display monitor at a typical 10 hertz (Hz) rate. In other embodiments, the video clip can be played at much higher rates as the person looks at the images and EEG measurements from standard EEG electrodes are recorded.

Figure 6:
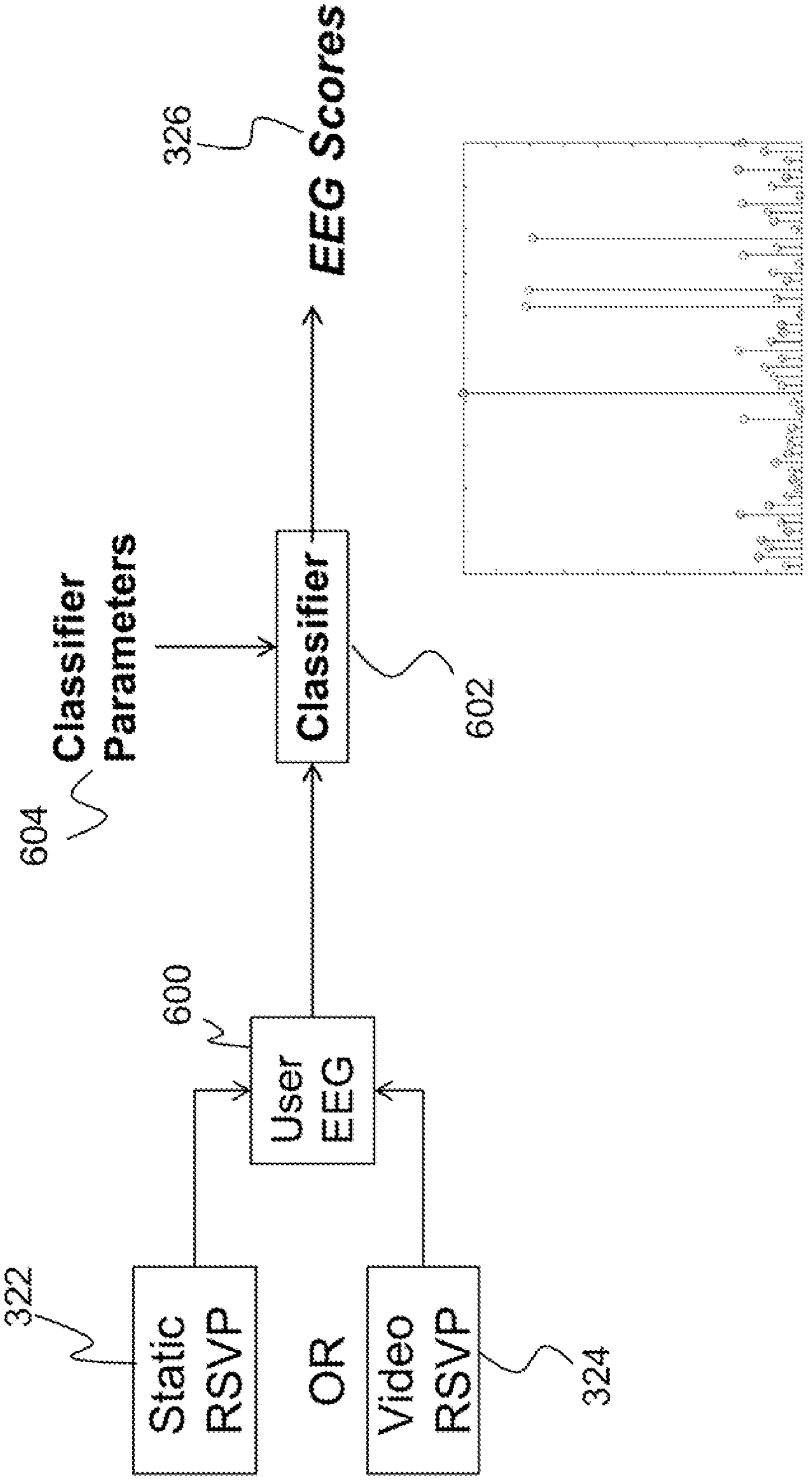
FIG. 6 is a flow diagram depicting a method for computing EEG scores according to the present invention.

Finally, the system is configured to compute an EEG score 326 as a final output. The user EEG measurements collected during RSVP presentation (sixth module 320) can be pre-processed via band-pass filtering in the desired frequency range (typically 1-100 Hz). Alternatively, results can be obtained without pre-processing. As shown in FIG. 6, the onset of presentation of each image (static case) or clip (video case) is also recorded, and this onset is used as a starting trigger to create user EEG 600 data segments (or epochs) from the EEG measurements. Each user EEG 600 data segment corresponds to each image presentation, is typically one second long, and contains the neural signatures of the desired visual response for that image presentation. Each user EEG 600 data segment is then classified into one of two classes: segments that contain an item of interest or segments that do not contain the item of interest. In practice, each user EEG 600 data segment is assigned a continuous score or likelihood of it belonging to each class.

The computation of an EEG score 326 includes an explicit prior training step during which known images or clips of targets and non-targets are presented and the learning of features and classifiers 602 in the corresponding user EEG 600 data segments is carried out. Thus, two classifiers 602 are learned: one for static datasets and one for video datasets. These classifiers 602 are them employed to determine an EEG score 326 for the specific type of RSVP presentation (static RSVP 322 or video RSVP 324). This learning can be done using a set of classifier parameters 604, non-limiting examples of which include time series analysis, feature extraction, and classification methods. In an embodiment described below, linear discrimination analysis of RSVP EEG data was used for classification of neural signatures into IOI and non-IOI regions or images.

Once the learning is complete, the learned classifier 602 is used for subsequent classification of the user EEG 600 data segments. Thus, each user EEG 600 data segment and its corresponding visual image is assigned a classification score, typically between 0 and 1, for each of the classes (i.e., item of interest or no item of interest). This score is the EEG score 326 and is the final score of the IOI. Based on the EEG score, the data segment (image chip) is classified 328 as containing an IOI or not containing an IOI. High classification scores indicate a high likelihood of belonging to that class, and vice versa. This is a common practice in all classifiers and a threshold can be chosen to achieve a desired trade-off between true detections and false alarms to generate traditional Receiver Operating Characteristics (ROC) performance curves, if desired. This step can optionally further sort the potential IOI regions in descending order (e.g., highest scores first) based on classification scores of the IOI class.

Figure 7:
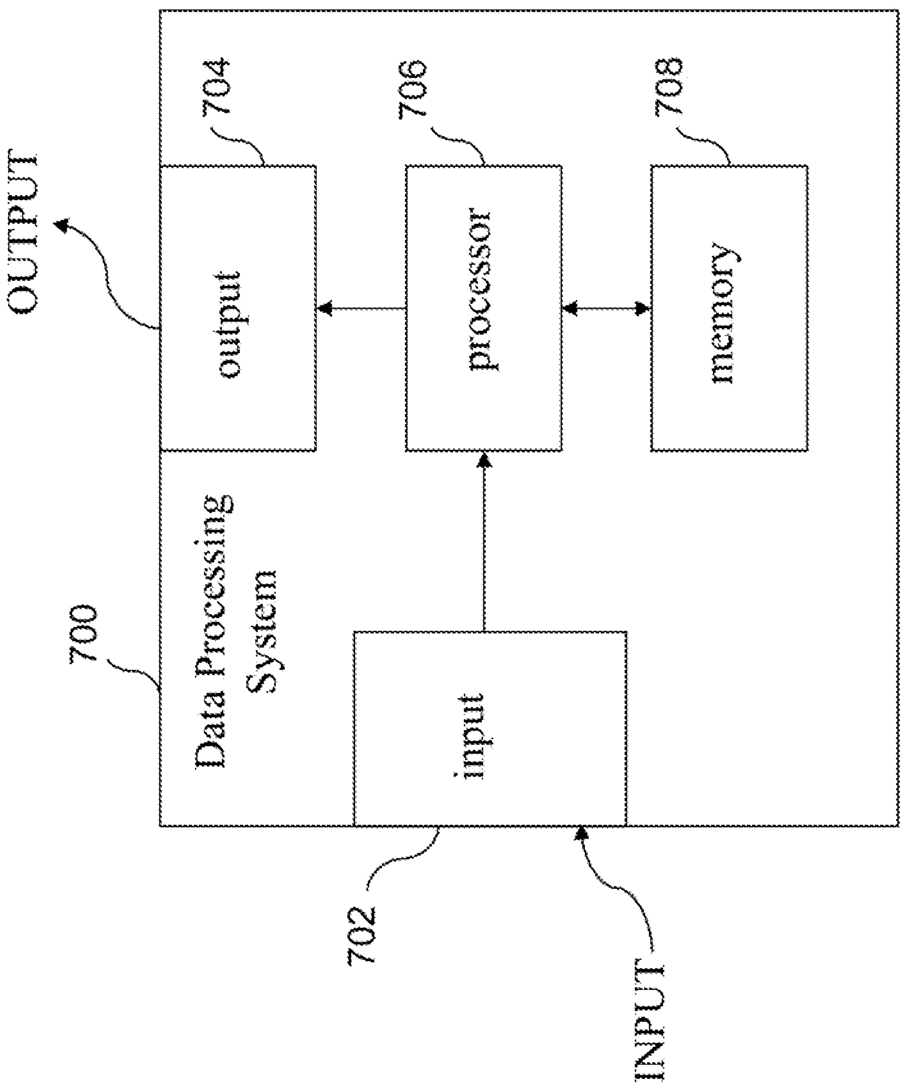
FIG. 7 is an illustration of a data processing system according to the present invention.

FIG. 7 illustrates a block diagram depicting components of a data processing system 700 (e.g., computer) incorporating the operations of the method described above and throughout the specification. The method utilizes a data processing system 700 for storing computer executable instructions (or instruction means) for causing a processor to carry out the operations of the above described method. The data processing system 700 comprises an input 702 for receiving information from a user. Information received may include input from devices such as cameras, scanners, keypads, keyboards, microphone, other peripherals such as storage devices, other programs, etc. The input 702 may include multiple "ports." An output 704 is connected with a processor 706 (or processors) for providing information for transmission to other data processing systems, to storage devices, to display devices such as monitors, to generating information necessary for delivery, and to other mechanisms for presentation in user-usable forms. The input 702 and the output 704 are both coupled with the processor 706, which may be a general-purpose computer processor or a specialized processor designed specifically for use with the present invention. The processor 706 is coupled with a memory 708 to permit storage of data and software to be manipulated by commands to the processor 706. The memory 708 includes instructions such that when the instructions are executed, the processor 708 (or processors) performs operations described above and throughout the specification.

Figure 8:
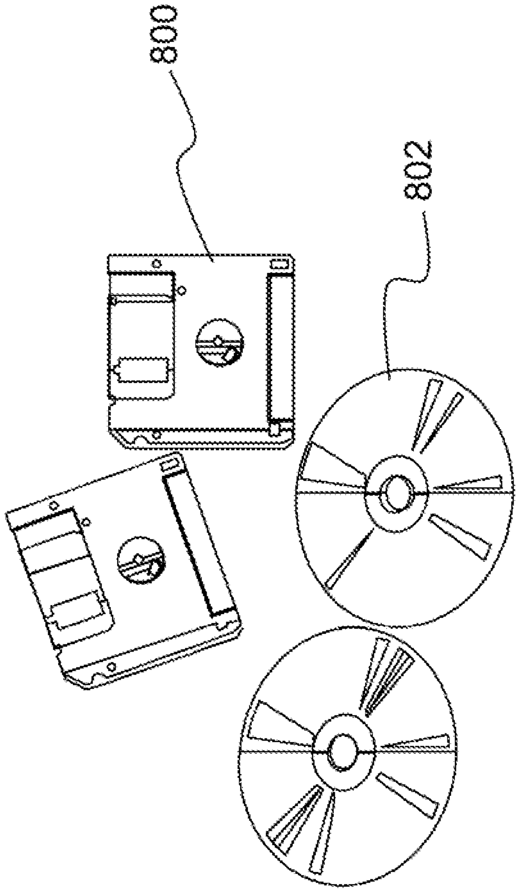
FIG. 8 is an illustration of a computer program product according to the present invention.

An illustrative diagram of a computer program product embodying the present invention is depicted in FIG. 8. As a non-limiting example, the computer program product is depicted as either a floppy disk 800 or an optical disk 802. However, as mentioned previously, the computer program product generally represents computer readable code (i.e., instruction means or instructions) stored on any compatible computer readable medium.

What is claimed is:

1. A system for optimizing rapid serial visual presentation, the system comprising:

one or more processors and a memory having instructions such that when the instructions are executed, the one or more processors perform operations of:

dividing an input image into a plurality of image chips;

computing a set of motion channel feature maps from the image chips;

computing a set of motion channel surprise maps from the set of motion channel feature maps;

labeling the image chips as static or moving;

preparing rapid serial visual presentation (RSVP) datasets of the image chips;

presenting RSVP datasets for visualization and recording of neural brain signals;

computing an electroencephalography (EEG) score from the neural brain signals based on a response to the image chips in the RSVP datasets; and classifying each image chip as containing an item of interest or not containing an item of interest based on the EEG score.

2. The system for optimizing rapid serial visual presentation as set forth in claim 1, wherein the one or more processors perform operations of:

creating at least one video clip by taking an image chip labeled as moving from a set of multiple consecutive image frames; and collecting all video clips into a RSVP video dataset.

3. The system for optimizing rapid serial visual presentation as set forth in claim 2, wherein the one or more processors perform operations of:

recording a neural brain signal upon an onset of presentation of a static image or a video clip;

creating an EEG data segment from the neural brain signal, wherein the EEG data segment is a neural signature of a desired visual response for the presentation of the static image or the video clip; and classifying the data segment as a data segment containing an item of interest or a data segment not containing an item of interest.

4. The system for optimizing rapid serial visual presentation as set forth in claim 3, wherein the one or more processors perform operations of:

receiving a set of known images of targets and a set of known images of non-targets for training;

learning of a classifier in a set of data segments which correspond to the set of known images of targets and the set of known images of non-targets;

wherein two distinct classifiers are learned for a static type RSVP dataset and a video type RSVP dataset; and employing the two distinct classifiers to determine an EEG score for each type of RSVP dataset presentation.

5. A computer-implemented method for optimizing rapid serial visual presentation comprising an act of:

causing a data processor to perform operations of:

dividing an input image into a plurality of image chips;

computing a set of motion channel feature maps from the image chips;

computing a set of motion channel surprise maps from the set of motion channel feature maps;

labeling the image chips as static or moving;

preparing rapid serial visual presentation (RSVP) datasets of the image chips;

presenting RSVP datasets for visualization and recording of neural brain signals;

computing an electroencephalography (EEG) score from the neural brain signals based on a response to the image chips in the RSVP datasets; and classifying each image chip as containing an item of interest or not containing an item of interest based on the EEG score.

6. The method for optimizing rapid serial visual presentation as set forth in claim 5, further comprising acts of:

creating at least one video clip by taking an image chip labeled as moving from a set of multiple consecutive image frames; and collecting all video clips into a RSVP video dataset.

7. The method for optimizing rapid serial visual presentation as set forth in claim 6, further comprising acts of:

recording a neural brain signal upon an onset of presentation of a static image or a video clip;

creating an EEG data segment from the neural brain signal, wherein the EEG data segment is a neural signature of a desired visual response for the presentation of the static image or the video clip; and classifying the data segment as a data segment containing an item of interest or a data segment not containing an item of interest.

8. The method for optimizing rapid serial visual presentation as set forth in claim 7, further comprising acts of:

receiving a set of known images of targets and a set of known images of non-targets for training;

learning of a classifier in a set of data segments which correspond to the set of known images of targets and the set of known images of non-targets;

wherein two distinct classifiers are learned for a static type RSVP dataset and a video type RSVP dataset; and employing the two distinct classifiers to determine an EEG score for each type of RSVP dataset presentation.

9. A computer program product for optimizing rapid serial visual presentation, the computer program product comprising:

computer-readable instruction means stored on a non-transitory computer-readable medium that are executable by a computer having a processor for causing the processor to perform operations of:

dividing an input image into a plurality of image chips;

computing a set of motion channel feature maps from the image chips;

computing a set of motion channel surprise maps from the set of motion channel feature maps;

labeling the image chips as static or moving;

preparing rapid serial visual presentation (RSVP) datasets of the image chips;

presenting prepared RSVP datasets for visualization and recording of neural brain signals;

computing an electroencephalography (EEG) score from the neural brain signals based on a response to the image chips in the RSVP datasets; and classifying each image chip as containing an item of interest or not containing an item of interest based on the EEG score.

10. The computer program product for optimizing rapid serial visual presentation as set forth in claim 9, further comprising instructions means for causing the processor to perform operations of:

creating at least one video clip by taking an image chip labeled as moving from a set of multiple consecutive image frames; and collecting all video clips into a RSVP video dataset.

11. The computer program product for optimizing rapid serial visual presentation as set forth in claim 10, further comprising instructions means for causing the processor to perform operations of:

recording a neural brain signal upon an onset of presentation of a static image or a video clip;

creating an EEG data segment from the neural brain signal, wherein the EEG data segment is a neural signature of a desired visual response for the presentation of the static image or the video clip; and classifying the data segment as a data segment containing an item of interest or a data segment not containing an item of interest.

12. The computer program product for optimizing rapid serial visual presentation as set forth in claim 11, further comprising instructions means for causing the processor to perform operations of:

receiving a set of known images of targets and a set of known images of non-targets for training;

learning of a classifier in a set of data segments which correspond to the set of known images of targets and the set of known images of non-targets;

wherein two distinct classifiers are learned for a static type RSVP dataset and a video type RSVP dataset; and employing the two distinct classifiers to determine an EEG score for each type of RSVP dataset presentation.

* * * * *